United States Patent
Tadini D'Annolfo et al.

(10) Patent No.: US 11,116,716 B2
(45) Date of Patent: Sep. 14, 2021

(54) COSMETIC ANTI-BLEMISH COMPOSITION, USE OF THE COMPOSITION, ANTI-BLEMISH TREATMENT METHOD AND APPLICATION DEVICE

(71) Applicant: Natura Cosméticos S.A., São Paulo (BR)

(72) Inventors: Kassandra Tadini D'Annolfo, São Paulo (BR); Priscila Carollo Moncayo, São Paulo (BR); Eduardo Alexandre De Oliveira Reis, São Paulo (BR); Fabiana Paes, São Paulo (BR); Ricardo Augusto Santos De Oliveira, São Paulo (BR); Daniela Zimbardi, São Paulo (BR)

(73) Assignee: Natura Cosméticos S.A., São Paulo (BR)

( * ) Notice: Subject to any disclaimer, the term of this patent is extended or adjusted under 35 U.S.C. 154(b) by 19 days.

(21) Appl. No.: 16/312,453

(22) PCT Filed: May 24, 2017

(86) PCT No.: PCT/BR2017/050126
§ 371 (c)(1),
(2) Date: Dec. 21, 2018

(87) PCT Pub. No.: WO2018/032073
PCT Pub. Date: Feb. 22, 2018

(65) Prior Publication Data
US 2019/0167559 A1    Jun. 6, 2019

(30) Foreign Application Priority Data
Aug. 17, 2016    (BR) .................. 102016019123-8

(51) Int. Cl.
| | | |
|---|---|---|
| *A61Q 19/08* | (2006.01) | |
| *A61Q 19/00* | (2006.01) | |
| *A61Q 1/00* | (2006.01) | |
| *A61K 8/97* | (2017.01) | |
| *A61K 8/9789* | (2017.01) | |
| *A61K 8/49* | (2006.01) | |
| *A61K 8/64* | (2006.01) | |
| *A61K 8/73* | (2006.01) | |

(52) U.S. Cl.
CPC .............. *A61K 8/97* (2013.01); *A61K 8/4953* (2013.01); *A61K 8/64* (2013.01); *A61K 8/735* (2013.01); *A61K 8/9789* (2017.08); *A61Q 19/00* (2013.01); *A61Q 19/08* (2013.01)

(58) Field of Classification Search
CPC ......... A61P 17/00; A61Q 19/08; A61Q 19/00; A61Q 19/02; A61Q 1/02; A61Q 19/008; A61Q 1/00; A61K 2300/00; A61K 9/0014; A61K 8/042; A61K 2800/10; A61K 38/011; A61K 45/06
See application file for complete search history.

(56) References Cited

U.S. PATENT DOCUMENTS

| | | | | |
|---|---|---|---|---|
| 2005/0019283 | A1* | 1/2005 | Nonaka | A61K 8/345 424/62 |
| 2007/0196318 | A1* | 8/2007 | Marini | A61K 8/97 424/74 |
| 2009/0306025 | A1* | 12/2009 | Lane | A61K 31/18 514/161 |
| 2010/0143515 | A1* | 6/2010 | Faller | A61K 8/553 424/766 |
| 2011/0117041 | A1* | 5/2011 | Chantal | A61K 8/375 424/64 |
| 2012/0034175 | A1* | 2/2012 | Yarosh | A61K 8/345 424/62 |
| 2014/0010769 | A1* | 1/2014 | Lomakin | A61K 8/25 424/59 |
| 2014/0242134 | A1* | 8/2014 | Khoshdel | A61K 8/25 424/401 |
| 2016/0331673 | A1* | 11/2016 | Ferritto | A61Q 1/02 |

FOREIGN PATENT DOCUMENTS

| | | | | |
|---|---|---|---|---|
| EP | 0326191 A1 | 8/1989 | | |
| JP | 2001/322940 A | 2/2003 | | |
| WO | WO-2012013776 A2 * | 2/2012 | ............. | A61Q 19/02 |
| WO | WO 2015/031971 A2 | 3/2015 | | |
| WO | WO-2015031971 A2 * | 3/2015 | ........... | A61K 8/9789 |

OTHER PUBLICATIONS

International Search report and written opinion for International Application No. PCT/BR2017/050126 dated Aug. 16, 2017.

* cited by examiner

Primary Examiner — Tracy Liu
(74) Attorney, Agent, or Firm — Alston & Bird LLP

(57) ABSTRACT

The present invention relates to cosmetic anti-blemish compositions in gel form that are particularly useful in the lightening of shadows and in the reduction of bags under the eyes.

17 Claims, 1 Drawing Sheet

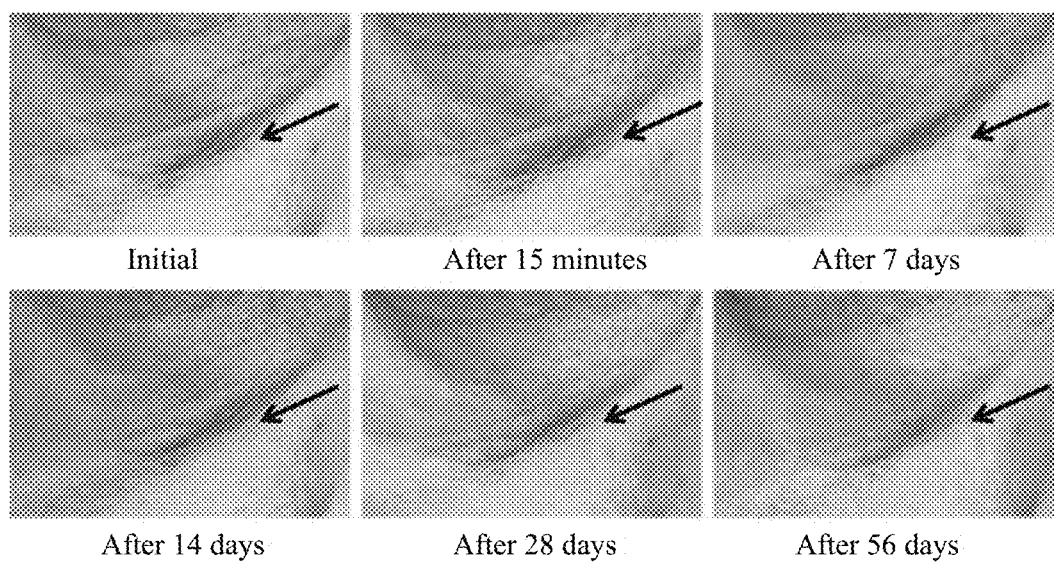

COSMETIC ANTI-BLEMISH COMPOSITION, USE OF THE COMPOSITION, ANTI-BLEMISH TREATMENT METHOD AND APPLICATION DEVICE

FIELD OF THE INVENTION

The present invention relates to super-concentrated cosmetic anti-sign compositions, in the form of an elixir, particularly useful in the treatment of wrinkles, especially in the area under eyes.

BACKGROUND

Dark eye circles and bags can appear in people of any age and sex and, as ultimate perception, end by imparting a fatigue and aging appearance to those people afflicted thereby.

Behavioral factors may cause or aggravate the problems, but there are other triggers for appearance of dark eye circles which include genetics, skin tone, respiratory allergies, flaccidity on the area, and fat accumulation under the skin of lower eyelids.

Moreover, as dark eye circles can be classified into three types:
(1) hyper-pigmented, which are dark spots around the eyes, as a result of blood stagnation in the area, that can purple or brown, the former being the most common type in light complexion, and the latter in darker complexion;
(2) deep dark eye circles, due to the eye anatomy, causing a kind of shading on the area; and (3) edematous, which constitute swelling of the eyelid, usually as a consequence of sleepless nights or stress.

The treatment for dark eye circles can be made by resting, but in some cases use of particularly invasive, combined treatments, such as peelings, carboxytherapy, laser, are required to achieve good lasting outcomes.

Therefore cosmetic compositions provably effective for clarifying dark eye circles and reducing bag under eyes are still desirable.

BRIEF DESCRIPTION OF THE FIGURES

FIG. 1 shows the results of bag reduction by applying the cosmetic composition according to the present invention.

DESCRIPTION OF THE INVENTION

The present invention relates to cosmetic anti-sign compositions, in the form of gel, which are particularly useful for clarifying dark eye circles and promptly and long-term reducing bag under eyes.

Surprisingly, effects on the clarification of dark eye circles and reduction of bag under eyes were found by using active compounds in combination, particularly *Schinus terebinthfolius* extract and *Coffea arabica* extract, acting on seven (7) main mechanisms responsible for formation of bags and dark eye circles:

1—Clarification of dark areas by tyrosinase inhibition;
2—Drainage stimulation and microcirculation improvement;
3—Blood vessel reinforcement and microcirculation improvement;
4—Antioxidant action;
5—Anti-hyaluronidase action;
6—Anti-lipoxygenase action.

*Coffea arabica* extract acts directly on microcirculation improvement and improve the lymphatic drainage process. Such action promotes an action on the process of bag formation. This action is further enhanced according to the present invention, for *Coffea arabica* is directed into a phospholipid complex.

*Schinus terebinthfolius* extract is rich in gallic acid, acting on the process of clarification of hyper-pigmentations (dark areas) by inhibiting the tyrosinase enzyme and reducing melanine, thereby clarifying the dark eye circles.

The cosmetic compositions according to the present invention provide a prompt and long-term treatment of bag under eyes and dark eye circles.

The cosmetic compositions according to the present invention allow an immediate masking bag under eyes and dark eye circles by average of light reflecting particles and low-coating pigments. Smoothing of bags is obtained by massaging them by using an applicator, a metal sphere that stimulates circulation in the area and causes a cooling effect.

Long-term speaking, the product acts by clarifying and reducing dark eye circles, reducing bag formation, and attenuating fatigue signs under the eyes, in addition to hydrating the area.

Therefore, the cosmetic anti-sign compositions according to the present invention are provided in the form of gel, comprising:
  a) at least one emollient;
  b) at least one antioxidant;
  c) at least one humectant;
  d) at least one active compound;
  e) at least one sensorial modifier; and
  f) cosmetically acceptable vehicles.

The emollient is selected from the group consisting of caprylyl methicone, a mixture of cetyl PEG/PPG-10/dimethicone 90, dicaprylyl carbonate, a mixture of dimethicone/trimethylsiloxysilicate, dodecane, polyglyceryl-4 isostearate, propylheptyl caprylate, alkyl benzoate having 12 to 15 carbons, dibutyl adipate, isononyl isononanoate, dicapryl ether, ethylhexyl palmitate, ethyl macadamiate, isohexadecane, capric/caprylic triglyceride, butters from the Brazilian biodiversity, isoamyl cocoate, or mixtures thereof, particularly caprylyl methicone, a mixture of cetyl PEG/PPG-10/dimethicone 90, dicaprylyl carbonate, a mixture of dimethicone/trimethylsiloxysilicate, dodecane, polyglyceryl-4 isostearate, propylheptyl caprylate, or mixtures thereof.

The antioxidant is selected from the group consisting of butylated hydroxytoluene (BHT), tocopherol acetate, or mixtures thereof.

The humectant is selected from the group consisting of glycerol, glycols, sorbitol, mannitol or mixtures thereof; particularly glycerol.

The active compound is selected from the group consisting of a mixture of caffeine/*Coffea arabica* extract/lecithin, *Camellia sinensis* extract, *Schinus terebinthfolius* extract, a mixture of sodium cocoyl amino acids/sarcosine/potassium aspartate/magnesium aspartate/propylene glycol, *Theobroma cacao* extract, a mixture of titanium dioxide/mica iron oxides/tin oxide, a mixture of water/butylene glycol/pantenol/escin/glycerine/*Ruscus Aculeatus* extract/ammonium glycyrrhizinate/*Centella Asiatica* extract/hydrolised yeast protein/*Calendula Officinalis* extract, acetyl tetrapeptide-2, *Hymenaea courbaril* extract, a mixture of *Paeonia albiflora* extract/phenoxyethanol/ethylhexylglycerine, *Cichorium intybus* extract, or mixtures thereof, particularly a mixture of caffeine/*Coffea arabica* extract/lecithin, *Camellia sinensis* extract, *Schinus terebinthfolius* extract, a mixture of sodium cocoyl amino acids/sarcosine/potassium aspartate/magnesium aspartate/propylene glycol, *Theobroma cacao* extract, a mixture of titanium dioxide/mica iron oxides/tin oxide, a mixture of water/butylene glycol/pantenol/escin/glycerine/*Ruscus Aculeatus* extract/ammonium glycyrrhizinate/*Centella Asiatica* extract/hydrolised yeast protein/*Calendula Officinalis* extract, or mixtures thereof.

The sensorial modifier is selected from the group consisting of silica, cyclopentasiloxano, dimethicone, titanio isopropil triisostearate, nylon-12, polimethylsilsesquioxano, or mixtures thereof, particularly silica.

The cosmetically acceptable vehicles can be selected from those compounds known in the art.

As examples of vehicles there can be mentioned: solvents, preservatives (such as phenoxyethanol and iodopropynyl butylcarbamate), perfumes/fragrances, polymer neutralizing agents, chelating agents (such as disodium EDTA), pH adjusting agents, and the like.

The active compound or a mixture of active compounds is present in the compositions according to the present invention in an amount from about 10 to about 20% by weight relative to the total weight of the composition, particularly about 14% of at least one active compound.

Additionally, the composition according to the present invention can comprise a viscosity donor selected from hectorite in glyceryl tri caprylate/caprate, carbopol, a mixture of hydroethylacrilato/sodium acryloyldimethyltaurate copolymer/squalane/polysorbate 60, or mixtures thereof, particularly hectorite in glyceryl tri caprylate/caprate.

Additionally, the composition according to the present invention can comprise a silicone selected from cyclopentasiloxane/dimethicone crospolymers e/ou pentylene glycol as a conditioning agent.

In a preferred embodiment, the composition according to the present invention can further comprise at least one pigment selected from titanium dioxide, mica, iron oxides, isopropyltitanium triisostearate, CI77491, CI77492, CI77499, CI77891, or mixtures thereof.

In a preferred embodiment, the pigments are selected from one or more of CI77491/Isopropyltitanium triisostearate (commercially available under the tradename BRO-I2 by Kobo Products), CI77492/Isopropyltitanium triisostearate (commercially available under the tradename BYO-I2 by Kobo Products), CI77499/Isopropyltitanium triisostearate (commercially available under the tradename BBO-I2 by Kobo Products), CI77891/Isopropyltitanium triisostearate (a mixture of titanium dioxide, mica and iron oxides, commercially available under the tradename KZT Xian Vistas by Cosmotec).

In another embodiment, the present invention also contemplates the use of the cosmetic compositions as described herein in anti-signs treatment or dark eye circles clarification and/or bag under eyes treatment.

In another embodiment, the present invention also contemplates a method for anti-sign treatment or a method for clarifying dark eye circles and/or treating bag under eyes, consisting of applying a cosmetically effective amount de a composition according to the present invention, to the area under the eyes, at least twice daily.

The present invention also contemplates an applicator device that is a roll-on containing the composition of the present invention.

The following examples, but without any limitation, illustrate the cosmetic anti-sign compositions according to the present invention, which surprisingly act, simultaneously, on 11 main mechanisms responsible for wrinkle formation, and provide an anti-sign and wrinkle filling effect on the area of the lips.

EXAMPLES

Example 1. Composition According to the Present Invention

The following table illustrates cosmetic compositions according to the present invention.

TABLE 1

Cosmetic anti-sign compositions

| Ingredient | Example A | Example B |
|---|---|---|
| Water | 44.978 | 43.91 |
| Hectorite in glyceryl tri caprylate/caprate (Bentone gel GTCC V) | 2 | 3.00 |
| BHT | 0.1 | 0.10 |
| *Coffea arabica* extract/Lecithin | 1 | 2.00 |
| *Camellia sinensis* extract | 0.001 | 0.001 |
| Caprylyl methicone | 6 | 4.00 |
| Cetyl PEG/PPG-10/1/dimethicone 90 | 2.5 | 1.50 |
| CI77491/isopropyltitanium triisostearate | 0.1 | 0.10 |
| CI77492/isopropyltitanium triisostearate | 0.5 | 0.40 |
| CI77499/isopropyltitanium triisostearate | 0.03 | 0.02 |
| CI77891/isopropyltitanium triisostearate | 3 | 4.00 |
| Cyclopentasiloxano/dimethicone crospolymer | 3 | 5.00 |
| Dicaprylyl carbonate | 2.5 | 3.00 |
| Dimethicone/trimethylsiloxysilicate | 1 | 0.80 |
| Disodium EDTA | 0.1 | 0.10 |
| Dodecane | 2 | 1.50 |
| Glycerine (glycerol) | 8 | 6.00 |
| Iodopropynyl butilcarbamato | 0.09 | 0.07 |
| Pentylene glycol | 1 | 2.00 |
| Phenoxyethanol | 0.8 | 0.60 |
| Polyglyceryl-4 isostearate | 3 | 5.00 |
| Propylheptyl caprylate | 10 | 7.00 |
| *Schinus terebinthfolius* extract | 0.35 | 0.45 |
| Silica (MSS-500W) | 2 | 3.00 |
| Sodium chloride | 0.75 | 0.55 |
| sodium cocoyl amino acids/sarcosine/potassium aspartate/magnesium aspartate/propylene glycol | 1.5 | 1.00 |
| *Theobroma cacao* extract | 0.001 | 0.001 |
| Titanium dioxide/Mica/Óxido de ferro/ Tin oxide | 0.5 | 0.80 |
| Tocopherol acetate | 0.2 | 0.10 |
| Water/Butylene Glycol/Pantenol/Escin/ Glycerine/*Ruscus Aculeatus* extract/ Glicirrizato de amônio/*Centella Asiatica* extract/hydrolised yeast protein/*Calendula Officinalis* extract | 3 | 4.00 |
| Total | 100.00 | 100.00 |

Example 2. Photographic Analysis of the Dark Eye Circles and Bags Under Eyes

The test consisted of an imaging analysis based on obtaining high resolution digital images before and after the product is applied, thus allowing a comparison between the images. The images were obtained at the beginning of the study, within 15 minutes after the first application, and after applying the composition at home for 7, 14, 28 and 56 days. The images were analyzed by using a specialized image analysis software, for determining the relative volume of suborbital swelling (bags) and the intensity of suborbital hyper-pigmentation (dark eye circles).

There was a significant average reduction in intensity of suborbital hyper-pigmentation (dark eye circles) of 6.3% after applying the composition at home for 28 days, and 8.4% for 56 days, as compared to the initial condition.

100% of the female volunteers in the research exhibited a reduction in intensity of suborbital hyper-pigmentation after applying the composition at home for 28 days and for 56 days.

There was a significant average reduction in intensity of suborbital swelling (bag under the eyes) by 1.8% after applying the composition at home for 14 days, 2.3% for 28 days, and 2.7% for 56 days, as compared to the initial condition.

80.0% of the female volunteers in the research exhibited a reduction in intensity of suborbital swelling after applying the composition at home for 14 days, and 85.0% of the volunteers exhibited a reduction in intensity of suborbital swelling after applying the composition at home for 28 and 56 days.

Example 3. Assessment of the Efficacy of a Cosmetic Product Through the Efficacy Perceived by a Volunteer in the Research and by Evaluating the Dermatological Clinical Efficacy Under Normal Conditions of Use The volunteers in the research were evaluated by a dermatologist at the beginning of the study (D0) for the criteria of admission and non-admission and were also evaluated at the end of the study for eventual reactions or discomforts experienced while using the product.

Those volunteers admitted in the research were clinically evaluated by a dermatologist for the initial condition of the face complexion and subsequently they were advised to fill in a self-evaluation questionnaire also related to the initial condition of the face complexion (D0).

Once admitted and the first questionnaire was completed, a supervised application of the product was performed on all participants.

Subsequent to the first application, assessments as to the perceived and clinical efficacy were carried out, by means of a questionnaire to be filled within 10 minutes after the product was applied at the Institute (Dimediato) and after a 7-, 14-, 28- and 56-day (+/−2 days) use of the product.

The volunteers in the research were advised to apply the product at home according to the instructions as provided, for 56 days (+/−2 days).

Female participants, aged 25-69 years (mean age of 56 years), exhibited grade II to V wrinkles and visible bag under eyes and dark eye circles.

Assessment of Perceived Efficacy:

Significant masking of "dark eye circles, bag under eyes and expression lines", and a "cooling effect" feeling were seen 10 minutes after application;

There was a perception in improvement of "wrinkles (deep lines) and expression lines/signs (fine lines), Dark eye circles, Bag under eyes and Healthy appearance" at D14, D28 and D56 as compared to D7;

There was a perception in improvement of "wrinkles (deep lines) and expression lines/signs (fine lines)", at D28 as compared to D14;

There was a perception in improvement of "wrinkles (deep lines), expression lines/signs (fine lines) and Bag under eyes" at D56 as compared to D14.

Dimediato:

73.2% of the volunteers in the research perceived "Masking of dark eye circles";

71.4% of the volunteers in the research perceived "Masking of bag under eyes";

69.6% of the volunteers in the research perceived "Masking of expression lines";

94.6% of the volunteers in the research experienced the "Cooling effect".

D7:

57% of the volunteers in the research reported a reduction of "Wrinkles (deep lines)";

59% of the volunteers in the research reported a reduction in "Expression lines/signs (fine lines)";

59% of the volunteers in the research reported a reduction in "Dark eye circles";

50% of the volunteers in the research reported a reduction in "Bag under eyes";

70% of the volunteers in the research reported an improvement in "Healthy appearance".

D14:

71% of the volunteers in the research reported a reduction in "Wrinkles (deep lines)";

77% of the volunteers in the research reported a reduction in "Expression lines/signs (fine lines)";

79% of the volunteers in the research reported a reduction in "Dark eye circles";

71% of the volunteers in the research reported a reduction in "Bag under eyes";

82% of the volunteers in the research reported an improvement in "Healthy appearance".

D28:

88% of the volunteers in the research reported a reduction in "Wrinkles (deep lines)";

89% of the volunteers in the research reported a reduction in "Expression lines/signs (fine lines)";

86% of the volunteers in the research reported a reduction in "Dark eye circles";

82% of the volunteers in the research reported a reduction in "Bag under eyes";

86% of the volunteers in the research reported an improvement in "Healthy appearance".

D56:

85% of the volunteers in the research reported a reduction in "Wrinkles (deep lines)";

82% of the volunteers in the research reported a reduction in "Expression lines/signs (fine lines)";

84% of the volunteers in the research reported a reduction in "Dark eye circles";

82% of the volunteers in the research reported a reduction in "Bag under eyes";

87% of the volunteers in the research reported an improvement in "Healthy appearance".

Assessment of Clinical Efficacy

As compared to time point D0:

An improvement in the features "Extent of dark eye circles, General appearance and Healthy appearance" at Dimediato time points and D7 as compared to time point D0 was seen;

An improvement in the features "Extent of dark eye circles, extent of bag under eyes, General appearance and Healthy appearance" at time points D14 and D28 as compared to time point D0 was seen;

An improvement in the features "Extent of wrinkles, extent of dark eye circles, extent of bag under eyes, General appearance and Healthy appearance" no tempo D56 as compared to time point D0 was seen.

As compared to Dimediato time point:

An improvement in the features "General appearance and Healthy appearance" at time points D14 and D28 as compared to Dimediato time point was seen;

An improvement in the features "Extent of dark eye circles", General appearance was seen; and "Healthy" appearance at time point D56 as compared to Dimediato time point.

As compared to time point D7:

An improvement in the features "Extent of dark eye circles, extent of bag under eyes, General appearance and Healthy appearance" at time points D14 and D28 as compared to time point D7 was seen;

An improvement in the features "Extent of wrinkles, extent of dark eye circles, General appearance and Healthy appearance" at time point D56 as compared to time point D7 was seen.

As compared to time point D14:

An improvement in the features "Extent of dark eye circles, General appearance and Healthy appearance" at time point D28 as compared to time point D14 was seen;

An improvement in the features "Extent of wrinkles, extent of dark eye circles, General appearance and Healthy appearance" at time point D56 as compared to time point D14 was seen.

As compared to time point D28:

An improvement in the features "General appearance and Healthy appearance" at time point D56 as compared to time point D28 was seen.

Example 4. Assessment of Skin Hydration by Using FTIR-ATR

Skin hydration was assessed post-application of the test product by using FTIR-ATR (Fourier Transform Infrared Spectroscopy using Attenuated Total Reflectance) technique.

16 participants completed the study; average age: 43±8 years. No adverse reactions were noticed or reported during the study.

By the time the volunteers in the research were recruited, they were advised to withdraw the use any cosmetic products on the forearms by 48 hours prior to the start of the study. At the day of the study, the recruited participants who attended the laboratory were informed by the researcher as to the procedures used in the study, ethical and legal aspects, risks and benefits, medical support, reimbursement of participation costs, and were asked to sign the TOLE ("written consent form") in duplicate. For the evaluation, two 2.5×5.0 cm sites were delimited on the right and left volar forearm of each participant, one site serving as a control (no products applied). Then, spectra of the skin under the initial condition (before the test product was applied) were acquired by using the red spectrophotometer (Frontier Model-PerkinElmer), having a ATR cell (PIKE Technologies) and a ZnSe crystal. Subsequently, the test product was applied and the participants remained at the lab for measurements to be taken within 15 minutes, 2, 4, 6, 8 hours post-application. Subsequent to the 8-hour measurement the participants went back home, and were advised not to wet or wash their forearms. The following day, they returned to the lab for the measurement at 24 hours post-application of the test product.

According to results, it could be found that application of the test product kept the skin hydrated for up to 8 hours, as compared to the control (no products applied to the skin). Application of the test product increased the hydration level by up to 24%. 100% of the participants exhibited improvement in skin hydration subsequent to application of the test product.

Based on the teachings provided in the disclosure of the invention and examples one skilled in the art would be able to appreciate the advantages of the invention and propose variations and alternative equivalent embodiments, without departing from the scope of the invention, as defined in the appended claims.

The invention claimed is:

1. A cosmetic anti-blemish composition, wherein the composition is a gel comprising:
   at least one emollient;
   at least one antioxidant selected from the group consisting of butylated hydroxytoluene (BHT), tocopherol acetate, and mixtures thereof;
   at least one humectant;
   an active compound comprising a combination of *Schinus terebinthifolius* extract and about 1-2% by weight of the composition of a mixture of caffeine/*Coffea arabica* extract/lecithin;
   optionally at least one additional active compound selected from the group consisting of *Camellia sinensis* extract, a mixture of sodium cocoyl amino acids/sarcosine/potassium aspartate/magnesium aspartate/propylene glycol, *Theobroma cacao* extract, a mixture of titanium dioxide/mica iron oxides/tin oxide, a mixture of water/butylene glycol/pantenol/escin/glycerine/*Ruscus aculeatus* extract/ammonium glycyrrhizinate/*Centella asiatica* extract/hydrolised yeast protein/*Calendula officinalis* extract, acetyl tetrapeptide-2, *Hymenaea courbaril* extract, a mixture of *Paeonia albiflora* extract/phenoxyethanol/ethylhexylglycerine, *Cichorium intybus* extract, and mixtures thereof;
   at least one sensorial modifier; and
   cosmetically acceptable vehicles.

2. The composition according to claim 1, wherein the emollient is selected from the group consisting of caprylyl methicone, a mixture of cetyl PEG/PPG-10/dimethicone 90, dicaprylyl carbonate, a mixture of dimethicone/trimethylsiloxysilicate, dodecane, polyglyceryl-4 isostearate, propylheptyl caprylate, alkyl benzoate having 12 to 15 carbons, dibutyl adipate, isononyl isononanoate, dicapryl ether, ethylhexyl palmitate, ethyl macadamiate, isohexadecane, capric/caprylic triglyceride, butters from Brazilian biodiversity, isoamyl cocoate, and mixtures thereof.

3. The composition according to claim 2, wherein the emollient is selected from the group consisting of caprylyl methicone, a mixture of cetyl PEG/PPG-10/dimethicone 90, dicaprylyl carbonate, a mixture of dimethicone/trimethylsiloxysilicate, dodecane, polyglyceryl-4 isostearate, propylheptyl caprylate, and mixtures thereof.

4. The composition according to claim 1, wherein the humectant is selected from the group consisting of glycerol, glycols, sorbitol, mannitol and mixtures thereof.

5. The composition according to claim 4, wherein the humectant is glycerol.

6. The composition according to claim 1, wherein the composition comprises from about 10 to about 20% of at least one active compound relative to the total weight of the composition.

7. The composition according to claim 1, wherein the composition comprises from about 14% of at least one active compound relative to the total weight of the composition.

8. The composition according to claim 1, further comprising a viscosity donor selected from hectorite in glyceryl tri caprylate/caprate, cross-linked acrylic acid polymers, a mixture of hydroxyethyl acrylate/sodium acryloyldimethyl-taurate copolymer/squalane/polysorbate 60, and mixtures thereof.

9. The composition according to claim 8, wherein the viscosity donor is hectorite in glyceryl tri caprylate/caprate.

10. The composition according to claim 1, further comprising a silicone selected from cyclopentasiloxane/dimethicone crospolymers.

11. The composition according to claim 1, further comprising pentylene glycol as a conditioning agent.

12. The composition according to claim 1, wherein the sensorial modifier is selected from the group consisting of silica, cyclopentasiloxane, dimethicone, titanium isopropyl triisostearate, nylon-12, polymethylsilsquioxane, and mixtures thereof.

13. The composition according to claim 12, wherein the sensorial modifier is silica.

14. The composition according to claim 1, further comprising at least one pigment selected from titanium dioxide, mica, iron oxides, tin oxide, isopropyltitanium triisostearate, CI77491, CI77492, CI77499, CI77891, and mixtures thereof.

15. A method of anti-blemish treatment, the method consisting of applying a cosmetically effective amount of a composition as defined in claim 1, to an area under eyes at least twice daily.

16. The method according to claim 15, wherein the method is used in the clarification of dark eye circles and/or treatment of bag under eyes.

17. An applicator device, wherein the device is a roll-on comprising a composition as defined in claim 1.

* * * * *